(12) United States Patent
Goto

(10) Patent No.: US 8,542,248 B2
(45) Date of Patent: Sep. 24, 2013

(54) X-RAY DETECTION APPARATUS AND INFORMATION PROCESSING METHOD

(75) Inventor: Tomohiro Goto, Machida (JP)

(73) Assignee: Canon Kabushiki Kaisha, Tokyo (JP)

( * ) Notice: Subject to any disclaimer, the term of this patent is extended or adjusted under 35 U.S.C. 154(b) by 770 days.

(21) Appl. No.: 12/536,957

(22) Filed: Aug. 6, 2009

(65) Prior Publication Data

US 2010/0053214 A1 Mar. 4, 2010

(30) Foreign Application Priority Data

Aug. 29, 2008 (JP) .................................. 2008-222792

(51) Int. Cl.
| | |
|---|---|
| *G09G 5/12* | (2006.01) |
| *G06F 3/0481* | (2013.01) |
| *G06F 3/0484* | (2013.01) |
| *G06F 19/00* | (2011.01) |
| *G06F 11/32* | (2006.01) |

(52) U.S. Cl.
CPC .......... *G06F 3/0481* (2013.01); *G06F 3/04845* (2013.01); *G06F 2200/1637* (2013.01); *G06F 19/321* (2013.01); *G06F 11/323* (2013.01)
USPC ........... 345/627; 345/619; 345/649; 345/629; 345/661

(58) Field of Classification Search
CPC .............. G06F 3/0481; G06F 3/04845; G06F 2200/1637; G06F 19/321; G06F 11/323
USPC .................. 345/672, 619, 627, 649, 629, 661
See application file for complete search history.

(56) References Cited

U.S. PATENT DOCUMENTS

| | | | | |
|---|---|---|---|---|
| 4,322,619 | A | * | 3/1982 | Nelson et al. ................... 378/62 |
| 5,093,852 | A | * | 3/1992 | Nishikawa et al. ............. 378/39 |
| 5,150,292 | A | * | 9/1992 | Hoffmann et al. ............ 600/431 |
| 5,297,037 | A | * | 3/1994 | Ifuku ................................ 378/8 |

(Continued)

FOREIGN PATENT DOCUMENTS

| | | |
|---|---|---|
| JP | 08-167047 | 6/1996 |
| JP | 11-053577 | 2/1999 |

(Continued)

OTHER PUBLICATIONS

Office Action issued by JPO on Mar. 12, 2013 in counterpart Japanese Patent Application No. 2008-222792.

(Continued)

*Primary Examiner* — Javid A Amini
(74) *Attorney, Agent, or Firm* — Fitzpatrick, Cella, Harper & Scinto

(57) ABSTRACT

An X-ray image diagnosis apparatus allows setting information indicating an object direction in a radiographed image without any errors. This invention is an X-ray detection apparatus which detects X-rays applied to an object and generates a radiographed image of the object. This apparatus includes a unit to display, in a display area, a symbol which has a form corresponding to the object and for which a vector representing a direction as a reference for the symbol is defined, a button to change the direction of the symbol displayed in the display area, and a unit to output information concerning the direction of the vector in association with a radiographed image of the object, when the direction of the symbol displayed in the display area is changed to match the direction of the object with the direction of the symbol displayed in the display area.

10 Claims, 15 Drawing Sheets

(56) References Cited

U.S. PATENT DOCUMENTS

| | | | |
|---|---|---|---|
| 5,668,845 A * | 9/1997 | Migita | 378/4 |
| 6,999,558 B2 * | 2/2006 | Okoda | 378/102 |
| 7,154,985 B2 * | 12/2006 | Dobbs et al. | 378/4 |
| 7,488,108 B2 * | 2/2009 | Pommi | 378/205 |
| 7,627,154 B2 * | 12/2009 | Luo et al. | 382/128 |
| 7,677,799 B2 * | 3/2010 | Jensen et al. | 378/205 |
| 2002/0191814 A1 * | 12/2002 | Ellis et al. | 382/103 |
| 2003/0031291 A1 * | 2/2003 | Yamamoto et al. | 378/41 |
| 2005/0020911 A1 * | 1/2005 | Viswanathan et al. | 600/424 |
| 2005/0271996 A1 * | 12/2005 | Sporbert et al. | 433/24 |
| 2006/0204067 A1 * | 9/2006 | Tuma et al. | 382/128 |
| 2006/0235669 A1 * | 10/2006 | Charbel et al. | 703/11 |
| 2007/0152179 A1 * | 7/2007 | Mair et al. | 250/584 |
| 2008/0107233 A1 * | 5/2008 | Sakaguchi et al. | 378/91 |
| 2008/0280247 A1 * | 11/2008 | Sachdeva et al. | 433/24 |
| 2009/0150184 A1 * | 6/2009 | Spahn | 705/3 |
| 2010/0128840 A1 * | 5/2010 | Cha | 378/4 |
| 2011/0269097 A1 * | 11/2011 | Sporbert et al. | 433/24 |
| 2011/0305378 A1 * | 12/2011 | Florent et al. | 382/130 |

FOREIGN PATENT DOCUMENTS

| | | | |
|---|---|---|---|
| JP | 2004-97543 | | 4/2004 |
| JP | 2010051737 A | * | 3/2010 |
| JP | 2010057532 A | * | 3/2010 |

OTHER PUBLICATIONS

Office Action issued by JPO on Mar. 12, 2013 in counterpart Japanese Patent Application No. 2008-222792, with partial translation.

* cited by examiner

F I G. 10

|     | X  | Y  | Z  |
|-----|----|----|----|
| (a) | +1 | +1 | +1 |
| (b) | -1 | +1 | -1 |
| (c) | -1 | -1 | +1 |
| (d) | +1 | -1 | -1 |
| (e) | +1 | -1 | +1 |
| (f) | +1 | +1 | -1 |
| (g) | -1 | +1 | +1 |
| (h) | -1 | -1 | -1 |

FIG. 11
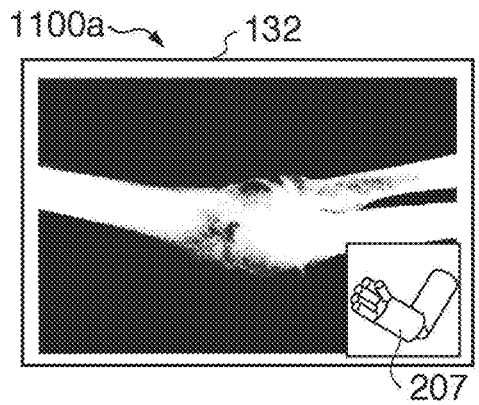
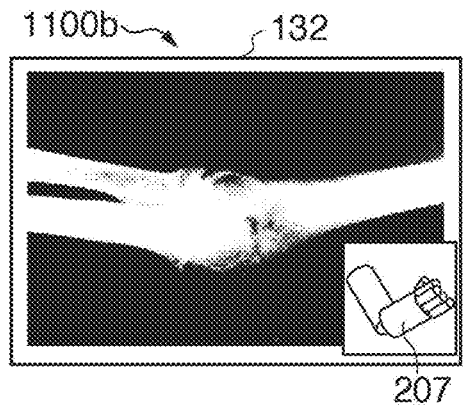
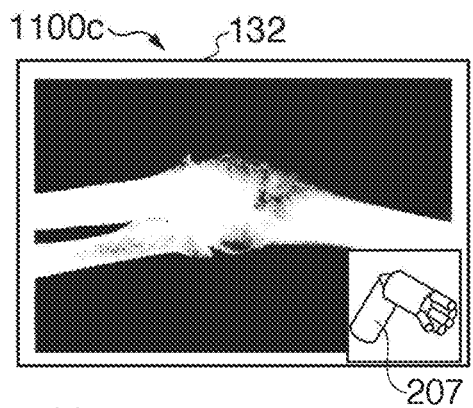
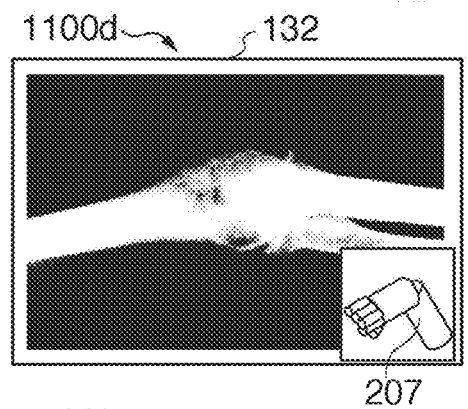
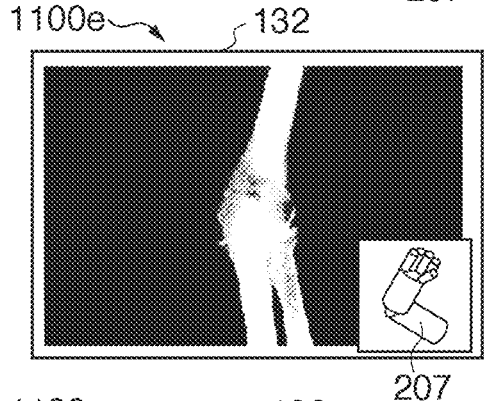
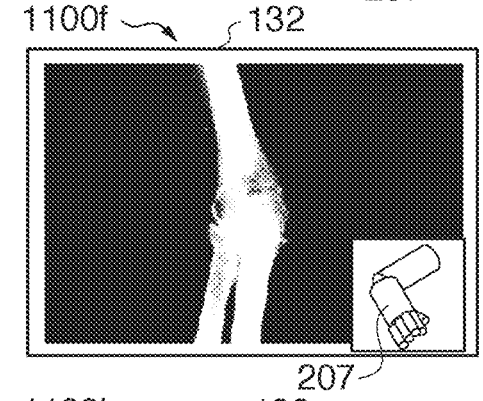
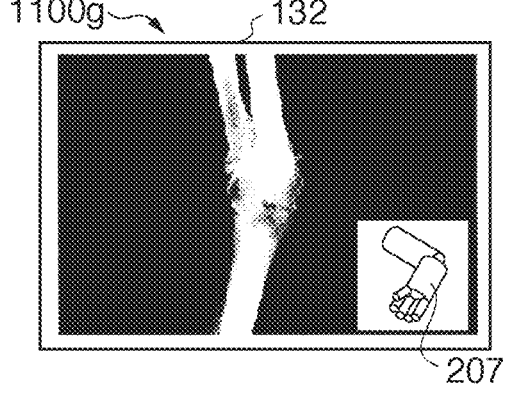
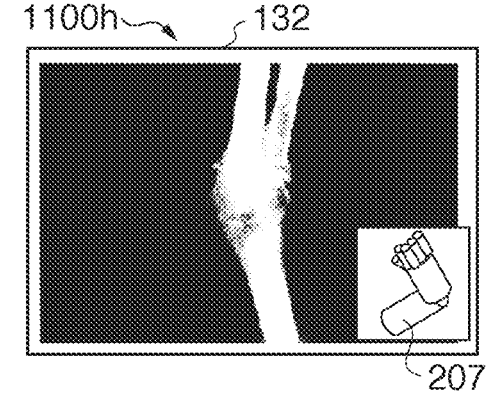

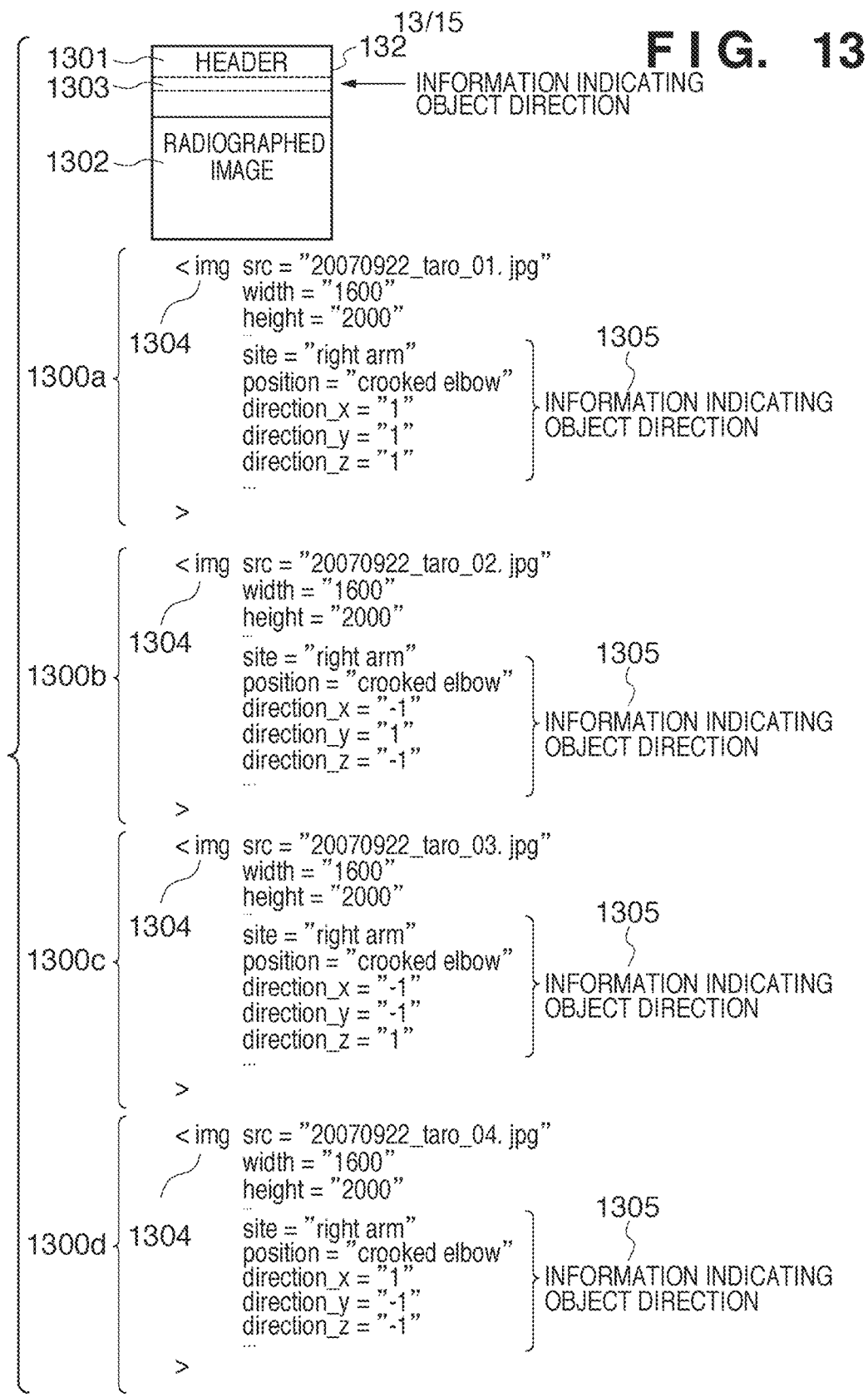

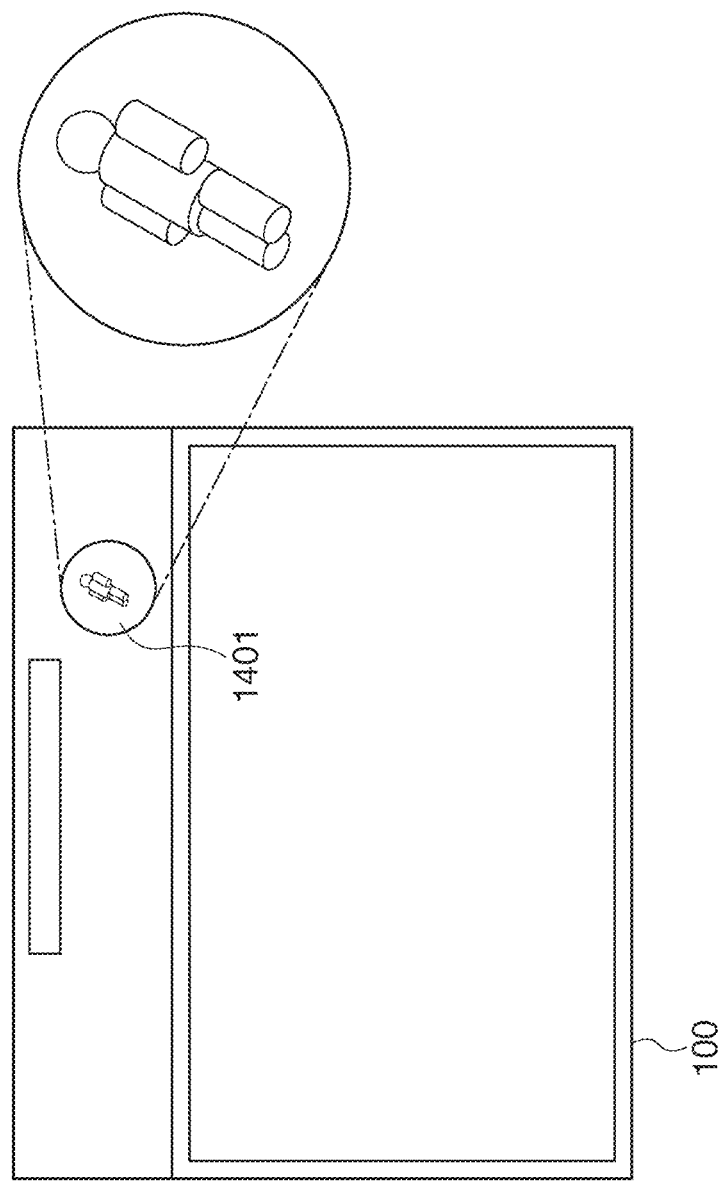

X-RAY DETECTION APPARATUS AND INFORMATION PROCESSING METHOD

BACKGROUND OF THE INVENTION

1. Field of the Invention

The present invention relates to an X-ray detection apparatus and, more particularly, to an information processing technique for setting information indicating the direction of a transmission image of an object in a radiographed image.

2. Description of the Related Art

Recently, in the field of X-ray image diagnosis apparatuses for medical uses, digital apparatuses using digital images have become popular in place of analog apparatuses using conventional X-ray films and intensifying screens.

A digital X-ray image diagnosis apparatus has the advantage of being capable of displaying radiographed images obtained by continuous X-ray imaging on a monitor, as moving images and storing them in a storage device such as a semiconductor memory or hard disk.

In both analog and digital systems, it is important for X-ray image diagnosis apparatuses to record in advance information indicating the direction of a transmission image of an object (to be referred to as an "object direction" hereinafter) in a radiographed image in association with the radiographed image.

A radiographed image obtained by an X-ray image diagnosis apparatus is a transmission image of an object. For this reason, if the direction in which the object faced relative to the X-ray detection apparatus during radiography cannot be determined, a doctor or other viewer may confuse (for example) the vertical and horizontal directions at the time of diagnosis.

Assume that X-ray imaging is performed on a person's chest as the object. In this case, an X-ray detection apparatus may be placed to the rear of the object, to irradiate the object with X-rays from the front of the object, or the X-ray detection apparatus may be placed in front of the object, to irradiate the object with X-rays from the rear of the object. In this case, the horizontal direction of a transmission image of the object in an obtained radiographed image reverses depending on the manner in which the X-ray imaging has been performed.

In addition, when X-ray imaging is to be performed on a portion of the body of a patient lying on a bed, the vertical direction of a transmission image of the object in an obtained image reverses depending upon the direction in which the patient's head is placed relative to the X-ray detection apparatus.

For this reason, in existing circumstances, X-ray imaging is performed using a marker for the discrimination of an object direction. This operation will be described in detail with reference to FIGS. 15A and 15B. FIG. 15B shows a radiographed image group obtained by X-ray imaging in various directions for an object 1501 attached with a marker by using an X-ray detection apparatus 1502 shown in FIG. 15A.

As shown in FIG. 15A, in general, a member made of a metal such as lead (to be referred to as a lead marker) which does not transmit X-rays is used as a marker, and a vertically and horizontally asymmetric symbol such as "L" or "R" is used. X-ray imaging is performed after the lead marker is attached to the object 1501 (or the X-ray detection apparatus 1502). With this operation, the radiographed image contains an image of the lead marker. This allows a doctor or other viewer to discriminate the object direction at the time of diagnosis.

FIG. 15A exemplifies a case in which X-ray imaging is performed on a person's chest. In this case, the obtained radiographed image is generally one of the eight types of images 1500a to 1500h shown in FIG. 15B.

On the other hand, with the widespread use of digital X-ray image diagnosis apparatuses, radiographed images are displayed on monitors mounted on X-ray image diagnosis apparatuses in more cases. In general, digitized radiographed images (radiographed image data) obtained by digital X-ray image diagnosis apparatuses are easy to process.

For this reason, a digital X-ray image diagnosis apparatus uses a method of embedding information (a symbol or graphic pattern) indicating an object direction in radiographed image data by performing so-called digital image processing after X-ray imaging.

According to this method, a doctor or other viewer determines an object direction by seeing the relative positions of the object and X-ray detection apparatus at the time of X-ray imaging, and manually sets the determination result.

It is, therefore, important for this method to minimize determination errors concerning object directions. In an X-ray image diagnosis apparatus or the like in which an X-ray detection apparatus is permanently installed on a dedicated bed or the like, some contrivance is made to always set the head of the patient in a specific direction relative to a bed. This makes the object direction always remain the same, and hence can reduce determination errors made by a doctor or other viewer when determining an object direction.

There has also been provided a method of automatically determining an object direction by extracting geometrical features of a transmission image of each region such as an organ, bone, or contour from a radiographed image by performing image processing for radiographed image data after X-ray imaging. This method automatically sets a determined object direction, and hence can minimize setting errors at the time of setting of determination results.

In addition, Japanese Patent Laid-Open No. 2004-97543 proposes an arrangement in which the radiographed image display unit of a digital X-ray image diagnosis apparatus is placed parallel to an X-ray detection apparatus through an object. This arrangement facilitates the determination of an object direction, and can reduce determination errors.

The various methods described above have various problems. For example, in the method of performing X-ray imaging for an image of a lead marker or the like, a character like "L" or "R" is used as a symbol. This may cause a placement error or read error due to a misjudgment or carelessness.

On the other hand, consider the method of making a doctor or the like determine an object direction by seeing the relative positions of an object and X-ray detection apparatus and embedding a symbol or graphic pattern corresponding to the determination result by so-called digital image processing. This method is free from the problem concerning marker placement errors, read errors, and the like. However, the method cannot avoid the possibility that a symbol or graphic pattern indicating an object direction may be set erroneously due to a determination error caused by a misjudgment by a doctor or other user, a setting error caused by carelessness, or the like.

For an object which is difficult to move to an X-ray room or sit up from the bed, X-ray imaging is performed after a transportable X-ray detection apparatus is installed depending on the object. In this case, the installation position of the X-ray detection apparatus changes for every X-ray imaging. This further increases the possibility of the occurrence of a determination error at the time of determination of an object direction and an input error at the time of setting of a determination result.

On the other hand, consider the method of automatically setting information indicating an object direction based on an estimation result obtained by automatically estimating an object direction upon extracting geometrical features of an image of a region such as an organ, bone, or contour by image processing of a radiographed image. This method is free from the problem of setting errors. The method, however, cannot accurately estimate an object direction concerning an object having a physical abnormality such as heterotaxy. That is, the method cannot prevent estimation results from containing estimation errors, and hence cannot be used without careful consideration.

SUMMARY OF THE INVENTION

The present invention has been made in consideration of the above problems.

An X-ray detection apparatus according to the present invention has the following arrangement. That is an X-ray detection apparatus which detects X-rays irradiated to an object and generates a radiographed image of the object, the apparatus comprising: a display unit configured to display, in a display area, a symbol which has a form corresponding to the object and for which a vector representing a direction as a reference for the symbol is defined; a changing unit configured to change the direction of the symbol displayed in the display area; and an output unit configured to output information concerning a direction of the vector relative to the X-ray detection apparatus in association with a radiographed image of the object, when the changing unit changes the direction of the symbol displayed in the display area to match the direction of the object with the direction of the symbol displayed in the display area.

According to the present invention, it is possible to set information indicating an object direction in a radiographed image in an X-ray image diagnosis apparatus without any errors.

Further features of the present invention will become apparent from the following description of exemplary embodiments with reference to the attached drawings.

BRIEF DESCRIPTION OF THE DRAWINGS

The accompanying drawings, which are incorporated in and constitute a part of the specification, illustrate embodiments of the invention and, together with the description, serve to explain the principles of the invention.

FIG. 10 is a view showing the coordinates of a reference vector when the direction of the symbol is operated;

FIG. 11 is a view showing an example of radiographed image data when postural information is added by a postural information adding unit;

FIG. 13 is a view showing an example of the data format of radiographed image data;

FIG. 14 is a view showing an outer arrangement of an X-ray detection apparatus.

DESCRIPTION OF THE EMBODIMENTS

Embodiments of the present invention will now be described in detail in accordance with the accompanying drawings.

First Embodiment

Arrangement of X-ray Detection Apparatus

Figure 1:
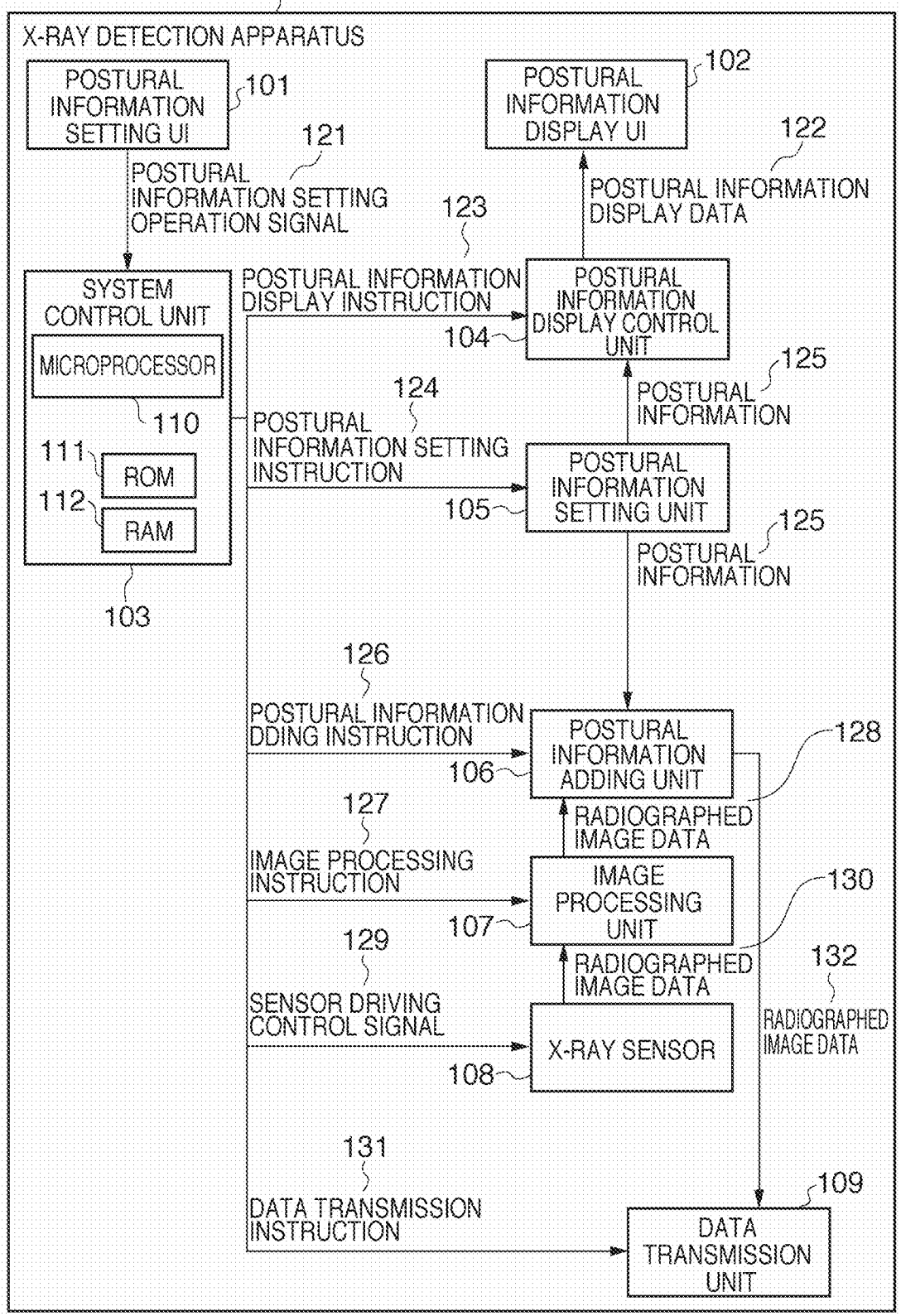
FIG. 1 is a block diagram showing the overall arrangement of an X-ray detection apparatus.

FIG. 1 is a block diagram showing the overall arrangement of an X-ray detection apparatus according to the first embodiment of the present invention. An X-ray detection apparatus 100 can form an X-ray image diagnosis apparatus by being communicatively connected to an X-ray image display apparatus (not shown).

As shown in FIG. 1, the X-ray detection apparatus 100 includes a postural information setting UI 101 and a postural information display UI 102. The X-ray detection apparatus 100 also includes a system control unit 103, a postural information setting unit 105, and a postural information display control unit 104. The X-ray detection apparatus 100 further includes an X-ray sensor 108, an image processing unit 107, a postural information adding unit 106, and a data transmission unit 109. Each unit will be described in detail below. Note that the postural information setting UI 101 and the postural information display UI 102 will be described in detail later.

The system control unit 103 includes a microprocessor 110 and a ROM (Read Only Memory) 111 storing control programs executed by the microprocessor 110. The system control unit 103 further includes a RAM (Random Access Memory) 112 used as a work area at the time of the execution of a control program.

When the postural information setting UI 101 transmits a postural information setting operation signal 121, the system control unit 103 outputs a postural information setting instruction 124 to the postural information setting unit 105. The system control unit 103 also outputs a postural information display instruction 123 to the postural information display control unit 104.

In addition, when an X-ray imaging start instruction (not shown) is transmitted, the system control unit 103 outputs a sensor driving control signal 129 to the X-ray sensor 108. The system control unit 103 also outputs an image processing instruction 127 to the image processing unit 107, and outputs a postural information adding instruction 126 to the postural information adding unit 106. Furthermore, the system control unit 103 outputs a data transmission instruction 131 to the data transmission unit 109.

The postural information setting unit 105 outputs set postural information (a region, a posture, symbol data, and the coordinates of a reference vector of the symbol data (to be described in detail later)) 125 to the postural information display control unit 104 and the postural information adding unit 106 based on the postural information setting instruction 124.

The postural information display control unit 104 outputs postural information display data 122 for making the postural information display UI 102 display the postural information 125 based on the postural information display instruction 123.

The X-ray sensor 108 includes a solid-state imaging device group to output electrical signals in accordance with the intensity of X-rays transmitted through an object. Alternatively, the X-ray sensor 108 includes a unit obtained by combining a phosphor which emits visible light in accordance with the energy of received X-rays and a photoelectric conversion element to output an electrical signal in accordance with the intensity of the visible light.

The X-ray sensor 108 operates in accordance with a data output timing signal generated based on the sensor driving control signal 129, and outputs radiographed image data 130. The radiographed image data 130 output from the X-ray sensor 108 is transmitted to the image processing unit 107.

The image processing unit 107 performs predetermined image processing for the radiographed image data 130 transmitted from the X-ray sensor 108 based on the image processing instruction 127. The predetermined image processing includes correction processing or noise removal processing dependent on the characteristics of the X-ray sensor 108 or processing for improving the quality of radiographed image, for example, dynamic range improvement processing. Radiographed image data 128 having undergone image processing in the image processing unit 107 is transmitted to the postural information adding unit 106.

Upon receiving the postural information adding instruction 126, the postural information adding unit 106 outputs radiographed image data 132 obtained by adding, to the radiographed image data 128, information (an image of symbol data or the coordinates of its reference vector) indicating an object direction contained in the postural information 125. The output radiographed image data 132 is transmitted to the data transmission unit 109.

Based on the data transmission instruction 131, the data transmission unit 109 transmits the radiographed image data 132, transmitted from the postural information adding unit 106, to an X-ray image display apparatus connected to a network or a file system which stores image data. The data transmission unit 109 executes packetization, network protocol processing, or the like for the radiographed image data 132.

<Arrangements of Postural Information Setting UI and Postural Information Display UI>

Figure 2:
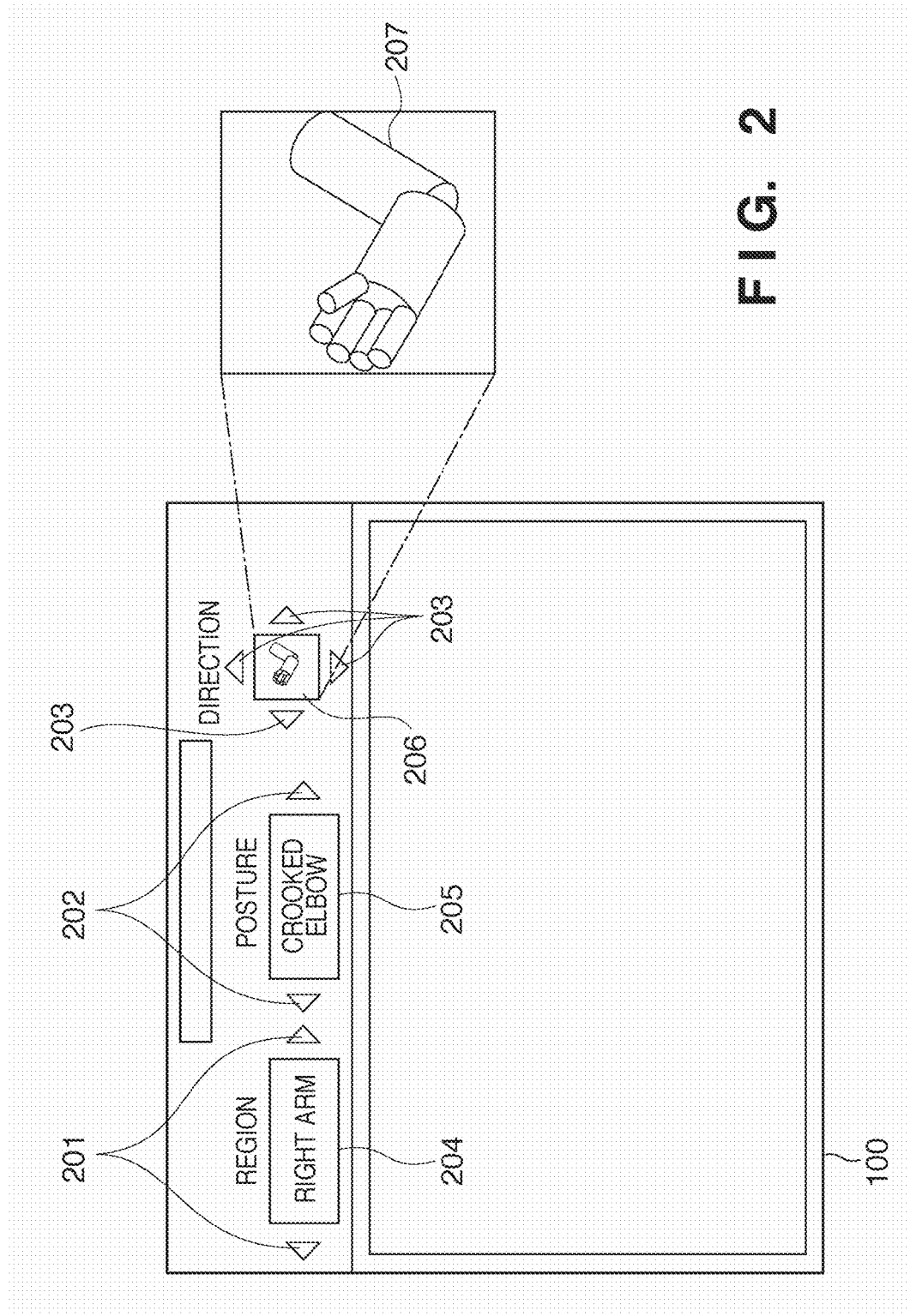
FIG. 2 is a view showing the outer arrangement of the X-ray detection apparatus.

FIG. 2 is a view showing the outer arrangement of an X-ray detection apparatus according to the first embodiment of the present invention. The arrangements of the postural information setting UI and postural information display UI will be described with reference to FIG. 2.

As shown in FIG. 2, the postural information setting UI 101 includes a region setting button 201, a posture setting button 202, and a direction setting button 203. The postural information display UI 102 includes a region display area 204, a posture display area 205, and a symbol data display area 206.

The region setting button 201 is a button to set a region of an object which is subjected to X-ray imaging. When an operator presses the region setting button 201, the region to be displayed in the region display area 204 is switched to another region. The operator can set a desired region by displaying it.

The name of a set region is displayed in the region display area 204. The regions to be displayed include, for example, "whole body", "head", "chest", "right arm", "left arm", "right leg", and "left leg".

The posture setting button 202 is a button for setting the posture of a region subjected to X-ray imaging. When the operator presses the posture setting button 202, the posture displayed in the posture display area 205 is switched to another posture. The operator can set a desired posture by displaying it.

Assume that the posture displayed in the posture display area 205 changes for each set region. For example, when "right arm" is set as such a region, "crooked elbow", "uncrooked elbow", or the like is displayed in the posture display area 205. When "whole body" is set as a region, a posture such as "standing", "sitting", or "lying" is displayed in the posture display area 205.

The direction setting button 203 is a button to change the direction of a symbol corresponding to an object in order to set information indicating an object direction which is the direction of a transmission image of the object which is specified by a set region and posture. The operator can change the direction of a symbol 207 by pressing the direction setting button 203.

Note that when, for example, "right arm" is set as a region and "crooked elbow" is set as a posture, the symbol 207 corresponding to the right arm (object) with the crooked elbow is displayed in the symbol data display area 206 in a predetermined direction.

As described above, the X-ray detection apparatus 100 according to this embodiment is configured to set information indicating an object direction by designating the direction of a symbol corresponding to the object (to be described in detail later).

Figure 3:
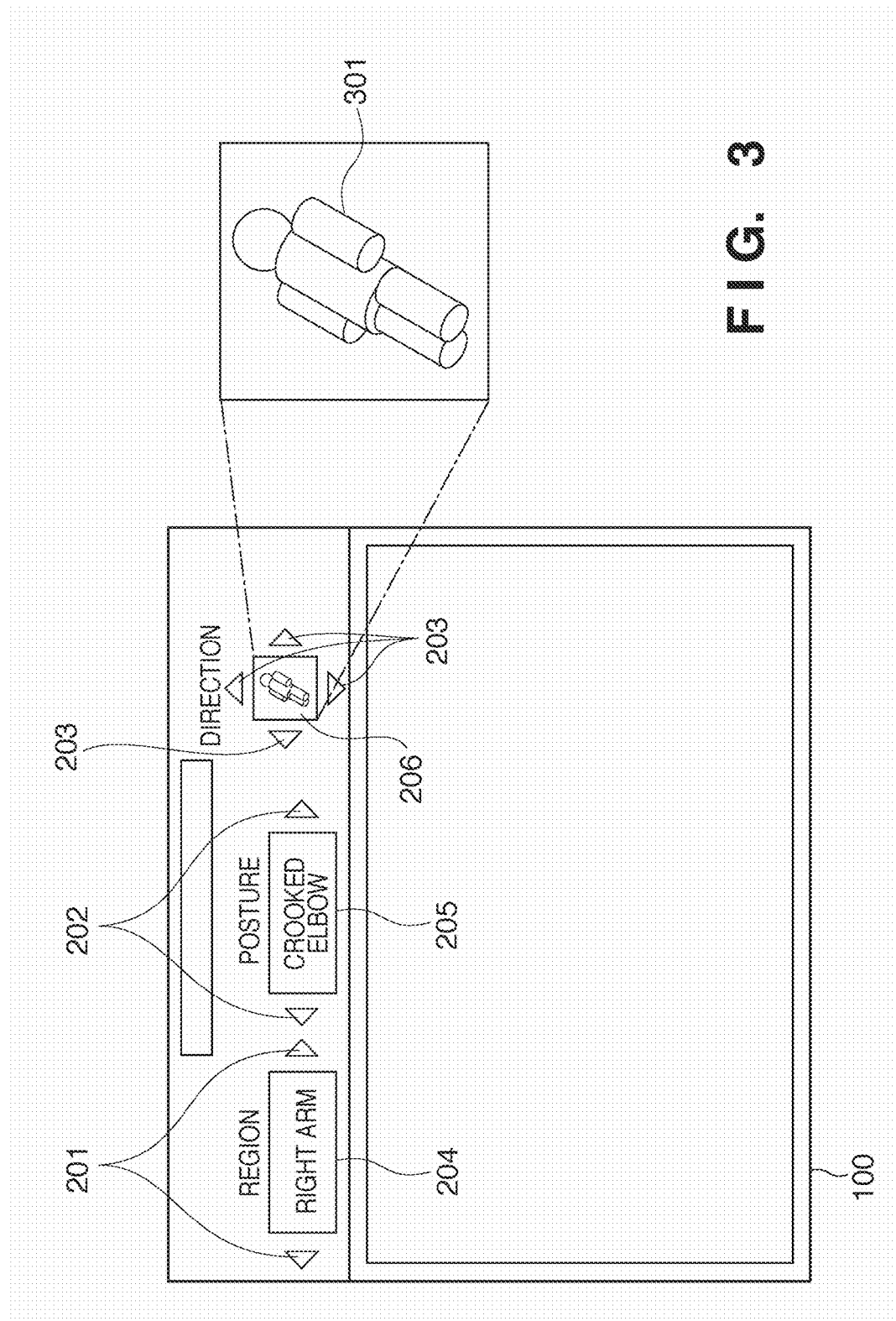
FIG. 3 is a view showing the outer arrangement of the X-ray detection apparatus.

FIG. 3 is a view showing the outer arrangement of the X-ray detection apparatus 100 and a state in which a region, a posture, and a direction different from those in FIG. 2 are set.

More specifically, "whole body" is set as a region, and "lying" is set as a posture. In the symbol data display area 206, a symbol corresponding to the whole body (object) in a lying state is displayed in the direction designated with the direction setting button 203.

As described above, the X-ray detection apparatus 100 according to this embodiment is configured to input a region of an object, a posture (object), and a symbol corresponding to the object to set the postural information 125.

<Direction of Object Relative to X-ray Detection Apparatus>

The definition of the direction of an object relative to the X-ray detection apparatus 100 will be described next with reference to FIGS. 4 to 6.

Figure 4:
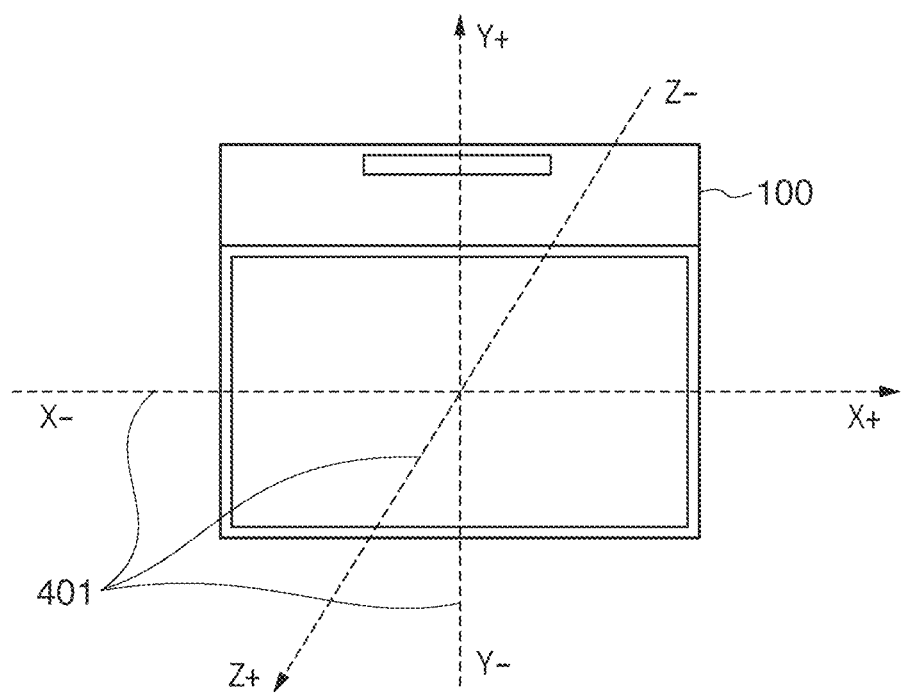
FIG. 4 is a view showing the coordinate axes of the X-ray detection apparatus.

FIG. 4 is a view showing the coordinate axes of the X-ray detection apparatus 100. As shown in FIG. 4, in the X-ray detection apparatus 100 according to this embodiment, coordinate axes 401 are defined such that the leftward and rightward directions are defined as the positive and negative directions of the X-axis; the upward and downward directions, as the positive and negative directions of the Y-axis; and directions perpendicular to the X-ray detection apparatus 100, as the positive and negative directions of the Z-axis.

Figure 5:
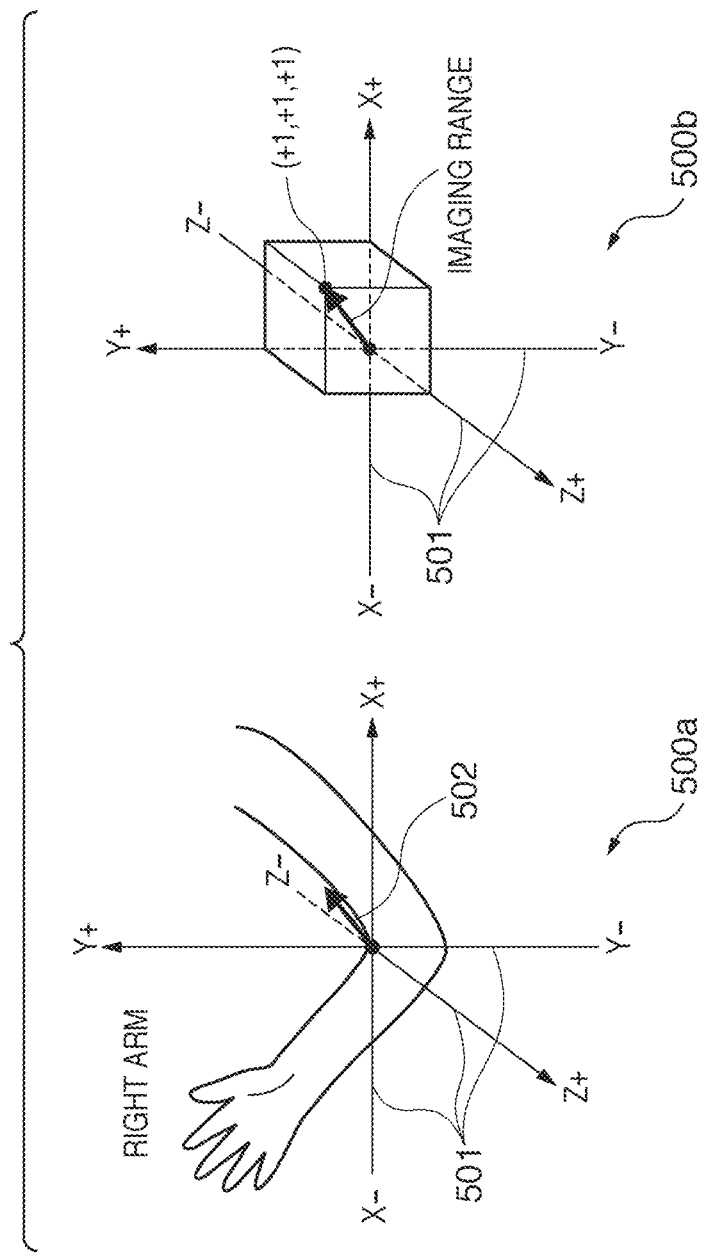
FIG. 5 is a view showing coordinate axes serving as references when the direction of an object is defined.

FIG. 5 is a view showing coordinate axes serving as references when the direction of the right arm (object) with the crooked elbow is defined. Referring to FIG. 5, assume that coordinate axes 501 are independent of the coordinate axes 401 of the X-ray detection apparatus 100, and are defined in advance for each object.

As indicated by "500a" in FIG. 5, the coordinate axes 501 are defined such that the central point of the object is set as the origin; the shoulder side, as the positive side of the X-axis; the hand side, as the negative side of the X-axis; the thumb side, as the positive side of the Y-axis; the little finger side, as the negative side of the Y-axis; the palm side, as the positive side of the Z-axis; and the back side of the hand, as the negative side of the Z-axis.

A vector connecting the origin of the coordinate axes 501 and coordinates (+1, +1, +1) is defined as a reference vector 502 of the object (the right arm with the crooked elbow). This definition makes it possible to express the direction of the object relative to the coordinate axes 401 of the X-ray detection apparatus 100 by using the reference vector 502.

More specifically, first of all, the reference vector 502 is obtained based on the coordinate axes 501 specified by the directions of an object (the right arm with the crooked elbow) actually placed on the X-ray detection apparatus 100 on the shoulder side, the hand side, the thumb side, the little finger side, the palm side, and the back side of the hand, respectively.

The coordinates of the reference vector 502 relative to the coordinate axes 401 of the X-ray detection apparatus 100 are obtained next. Obtaining the coordinates of the reference vector 502 relative to the coordinate axes 401 of the X-ray detection apparatus 100 in this manner makes it possible to quantitatively express the direction of the object relative to the X-ray detection apparatus 100.

<Manner of Obtaining Coordinates of Reference Vector of Object Relative to X-ray Detection Apparatus>

As described above, it is possible to quantitatively express the direction of each object by defining coordinate axes and a reference vector in advance, which serve as references when the direction of each object is defined, and obtaining the coordinates of the reference vector when the object is placed on the X-ray detection apparatus 100.

It is, however, difficult in practice to obtain the reference vector 502 from the object placed on the X-ray detection apparatus 100 and obtain the coordinates of the reference vector 502 relative to the coordinate axes 401 of the X-ray detection apparatus 100.

The X-ray detection apparatus 100 according to this embodiment therefore implements this by using a symbol corresponding to an object.

More specifically, the operator operates the symbol displayed in the symbol data display area 206 to match its direction with that of the object actually placed on the X-ray detection apparatus 100. The coordinates of the reference vector 502 of the object are then indirectly obtained by calculating the coordinates of the reference vector of the symbol when the direction of the object actually placed on the X-ray detection apparatus 100 coincides with the direction of the symbol displayed in the symbol data display area 206.

For this purpose, the coordinate axes and reference vector of the symbol are defined in advance as in the same manner for the corresponding object.

Figure 6:
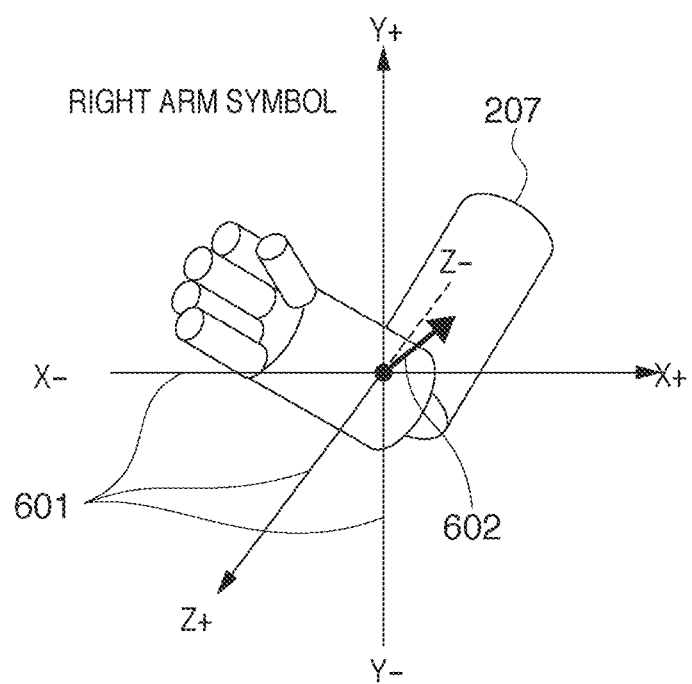
FIG. 6 is a view showing a symbol displayed in a symbol data display area, and coordinate axes and reference vector serving as references when the direction of the symbol is defined.

FIG. 6 is a view showing the symbol 207 displayed in the symbol data display area 206, and coordinate axes and a reference vector which serve as references when the direction of the symbol is defined, when "right arm" is set as a region and "crooked elbow" is set as a posture.

As shown in FIG. 6, coordinate axes 601 are defined such that the central point of the symbol 207 is set as the origin; the shoulder side, as the positive side of the X-axis; the hand side, as the negative side of the X-axis; the thumb side, as the positive side of the Y-axis; the little finger side, as the negative side of the Y-axis; the palm side, as the positive side of the Z-axis; and the back side of the hand, as the negative side of the Z-axis.

The direction of a vector connecting the origin of the coordinate axes 601 and coordinates (+1, +1, +1) is defined as a reference vector 602 of the symbol 207. This definition makes it possible to express the direction of the object relative to the coordinate axes 401 of the X-ray detection apparatus 100 by using the coordinates of the reference vector 602 of the symbol 207.

<Operation Procedure for Setting Information Indicating Object Direction>

As described above, the X-ray detection apparatus 100 according to this embodiment obtains the coordinates of a reference vector of a corresponding symbol to obtain the coordinates of a reference vector of an object and quantitatively express the direction of the object.

For this purpose, the operator of the X-ray detection apparatus 100 according to this embodiment operates the direction of the symbol to match the direction of the symbol displayed in the symbol data display area 206 with the direction of the object actually placed on the X-ray detection apparatus 100.

An operation procedure for this operation will be described with reference to FIGS. 7 and 8.

Figure 7:
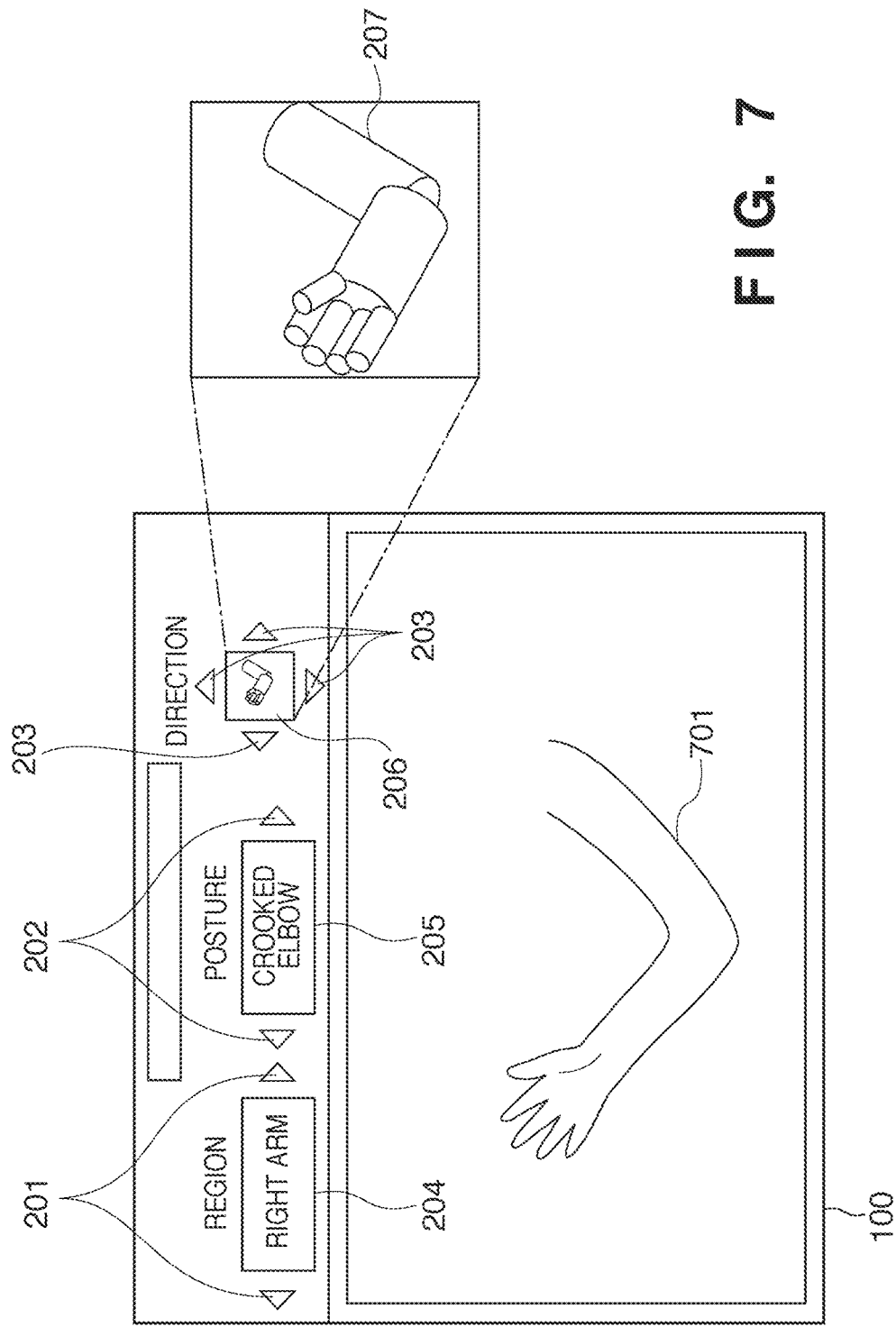
FIG. 7 is a view for explaining an operation procedure when information indicating the direction of an object is set.

FIG. 7 is a view for explaining an operation procedure for X-ray imaging of a right arm with a crooked elbow as an object.

As shown in FIG. 7, the operator selects "right arm" and "crooked elbow" as a region and a posture, respectively. In addition, the operator presses the direction setting button 203 to change the direction of the symbol 207 to match it with the direction of the object 701 placed on the X-ray detection apparatus 100.

The operator can set information indicating the direction of an object by intuitive operation because it suffices to press the direction setting button 203 to orient the symbol 207 designed after the form of the object in the same direction as that of the object.

Figure 8:
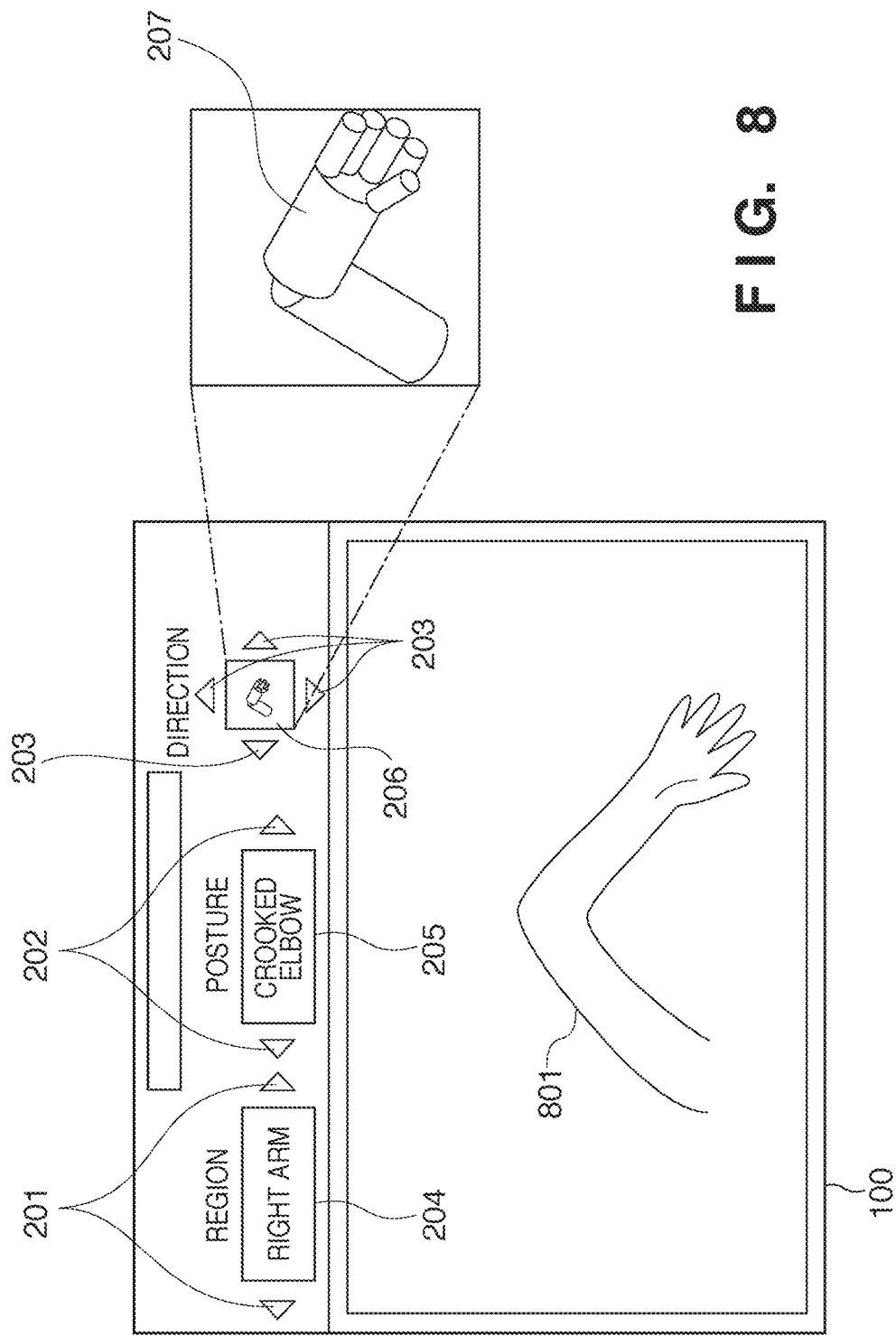
FIG. 8 is a view for explaining an operation procedure when information indicating the direction of an object is set.

FIG. 8 is a view for explaining an operation procedure for X-ray imaging of a right arm with a crooked elbow as an object. The difference from FIG. 7 is that the vertical direction of an object 801 is inverted.

In this case, as in the case in FIG. 7, after selecting a region and a posture, the operator changes the direction of the symbol 207 by pressing the direction setting button 203 to match its direction with the direction of the object 801 placed on the X-ray detection apparatus 100.

In this case, even if the vertical direction of the object is reversed, the operator matches the direction of the symbol 207 with the direction of the object 801 actually placed on the X-ray detection apparatus 100. That is, the operator need not determine the relative positions of the object 801 and X-ray detection apparatus 100, and hence is free from determination errors at the time of the determination of an object direction.

In addition, only pressing the direction setting button 203 can set information indicating an object direction (symbol data and the coordinates of its reference vector). This makes it possible to reduce setting errors and the like.

<Concrete Example of Coordinates of Reference Vector of Symbol>

A concrete example of the coordinates of a reference vector of the symbol 207 relative to the coordinate axes 401 will be described next.

Figure 9:
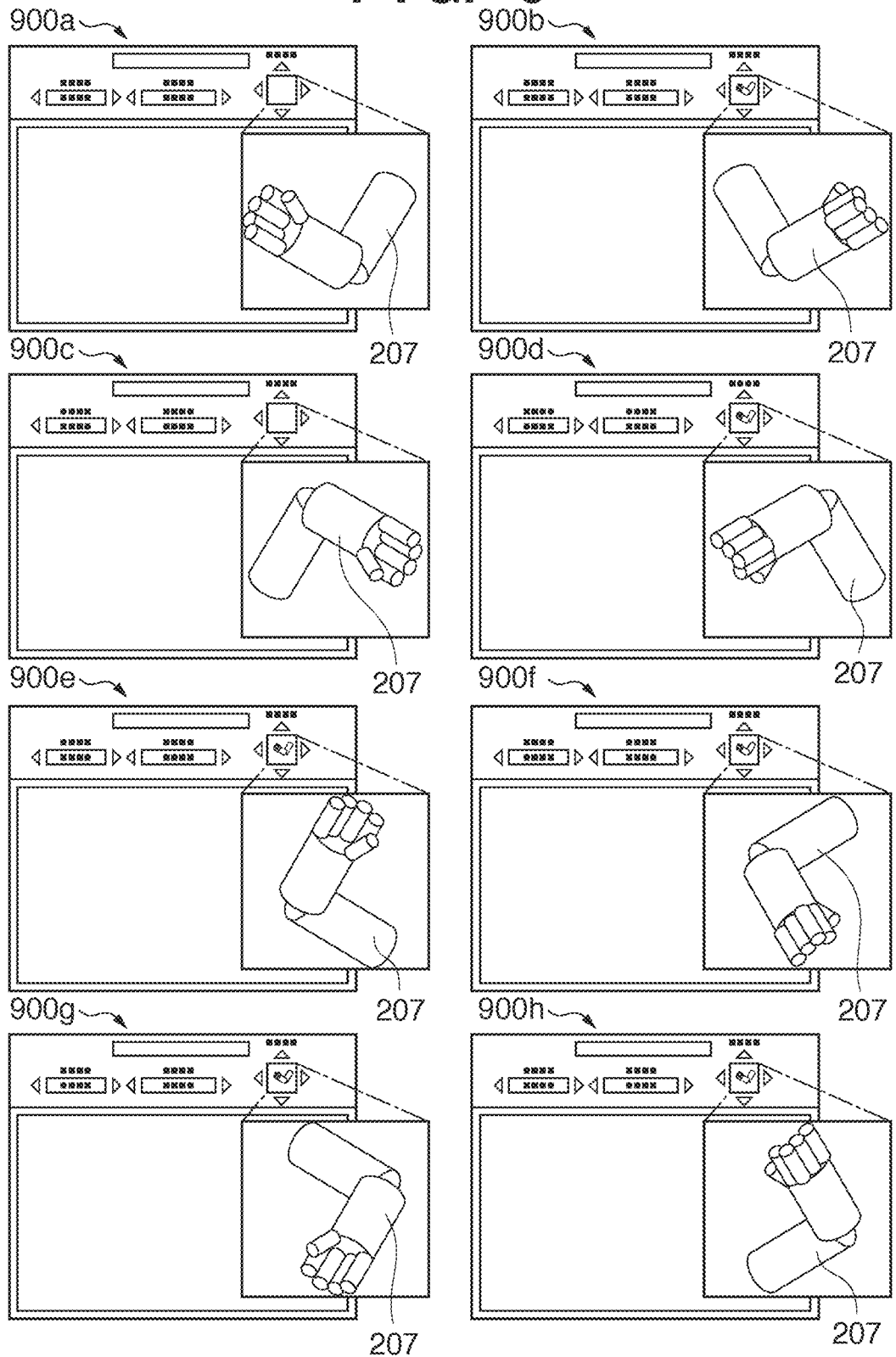
FIG. 9 is a view showing various directions of a symbol.

"900a" to "900h" in FIG. 9 indicate various directions of the symbol 207 when "right arm" and "crooked elbow" are set as a region and a posture, respectively. In addition, "(a)" to "(h)" in FIG. 10 indicate the coordinates of the reference vector 602 relative to the coordinate axes 401 when the direction of the symbol 207 is operated as indicated by "900*a*" to "900*h*" in FIG. 9.

For example, in the case indicated by "900*a*" in FIG. 9, since all the X, Y, and Z directions of the coordinate axes 401 of the X-ray detection apparatus 100 coincide with those of the coordinate axes 601 of the symbol, the coordinates of the reference vector 602 of the symbol 207 relative to the coordinate axes 401 become (+1, +1, +1) ("(a)" in FIG. 10).

In the case indicated by "900*b*" in FIG. 9, the X, Y, and Z directions of the coordinate axes 401 of the X-ray detection apparatus 100 coincide with those of the coordinate axes set by rotating the coordinate axes 601 of the symbol 207 about X-axis through 180° within the X-Y plane and about the Z-axis through 180° within the Z-X plane. Therefore, the coordinates of the reference vector 602 of the symbol 207 relative to the coordinate axes 401 become (−1, +1, −1) ("(*b*)" in FIG. 10).

In the case indicated by "900*e*" in FIG. 9, the X, Y, and Z directions of the coordinate axes 401 of the X-ray detection apparatus 100 coincide with those of the coordinate axes set by rotating the coordinate axes 601 of the symbol 207 about X-axis through 270° within the X-Y plane and about the Y-axis through 270° within the X-Y plane. Therefore, the coordinates of the reference vector 602 of the symbol 207 relative to the coordinate axes 401 become (+1, −1, +1) ("(*e*)" in FIG. 10).

In this manner, in the X-ray detection apparatus 100 according to this embodiment, operating the direction of the symbol will set symbol data and coordinates like those shown in FIG. 9 as information indicating an object direction.

<Method of Outputting Set Postural Information>

Of the information indicating the object direction contained in the postural information 125 set via the postural information setting UI 101, symbol data is output after being added to the radiographed image data 128 by the postural information adding unit 106.

FIG. 11 is a view showing an example of the radiographed image data 132 to which the symbol data contained in the postural information 125 is added by the postural information adding unit 106.

Referring to FIG. 11, reference numeral 207 denotes an image of the symbol data contained in the postural information 125. As shown in FIG. 11, the X-ray detection apparatus 100 according to this embodiment outputs the image of the symbol data upon superimposing it on corresponding radiographed image data.

As is obvious from the above description, this embodiment is configured to display a symbol corresponding to an object and make the operator operate the symbol to match its direction with the direction of the actual object on the X-ray detection apparatus when setting information indicating an object direction.

This arrangement configured to set information indicating an object direction by intuitive operation allows the operator to perform setting without any errors.

Second Embodiment

The first embodiment has exemplified about the coordinate axes and the reference vector when the object is "right arm with crooked elbow". Obviously, however, the object whose coordinate axes and reference vector are defined is not limited to "right arm with crooked elbow".

Figure 12:
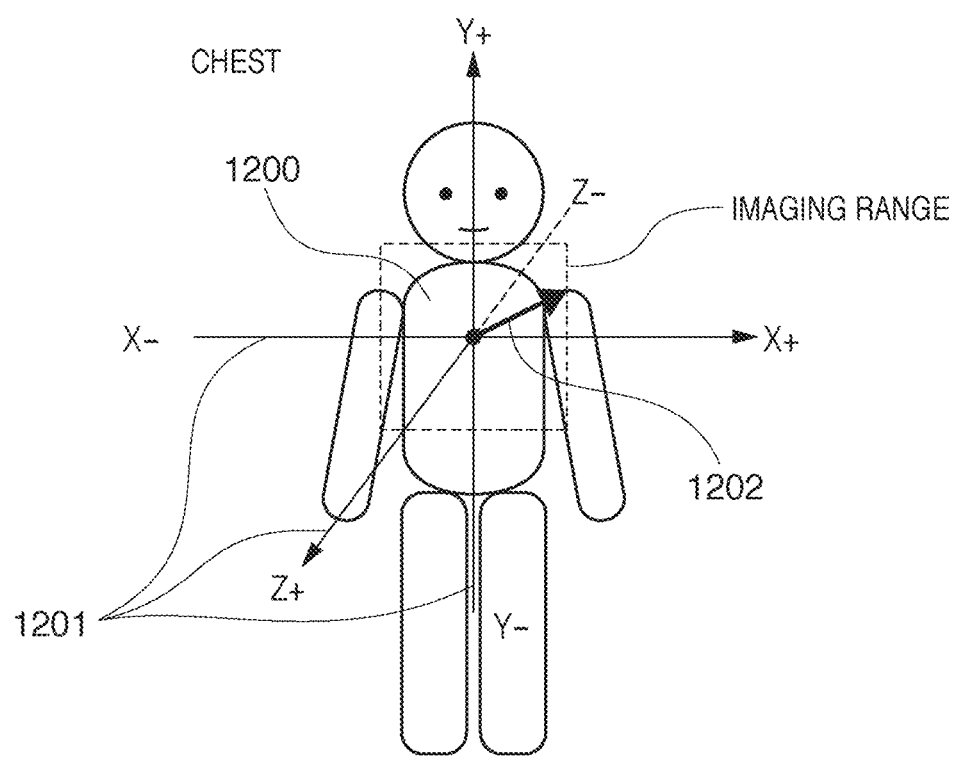
FIG. 12 is a view showing examples of the definitions of coordinate axes and reference vector.
Figure 15A:
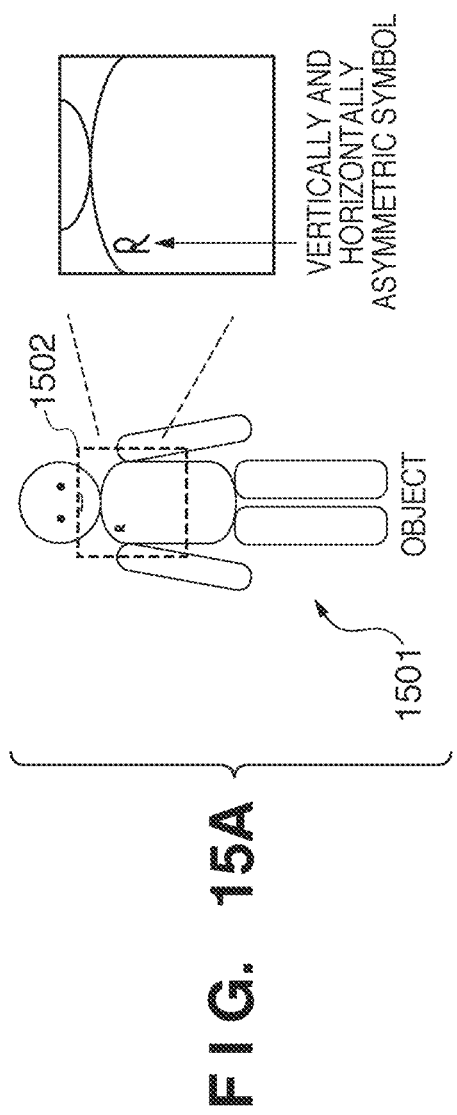
FIGS. 15A and 15B are views showing a radiographed image group when X-ray imaging is performed in various directions for an object with a marker attached.
Figure 15B:
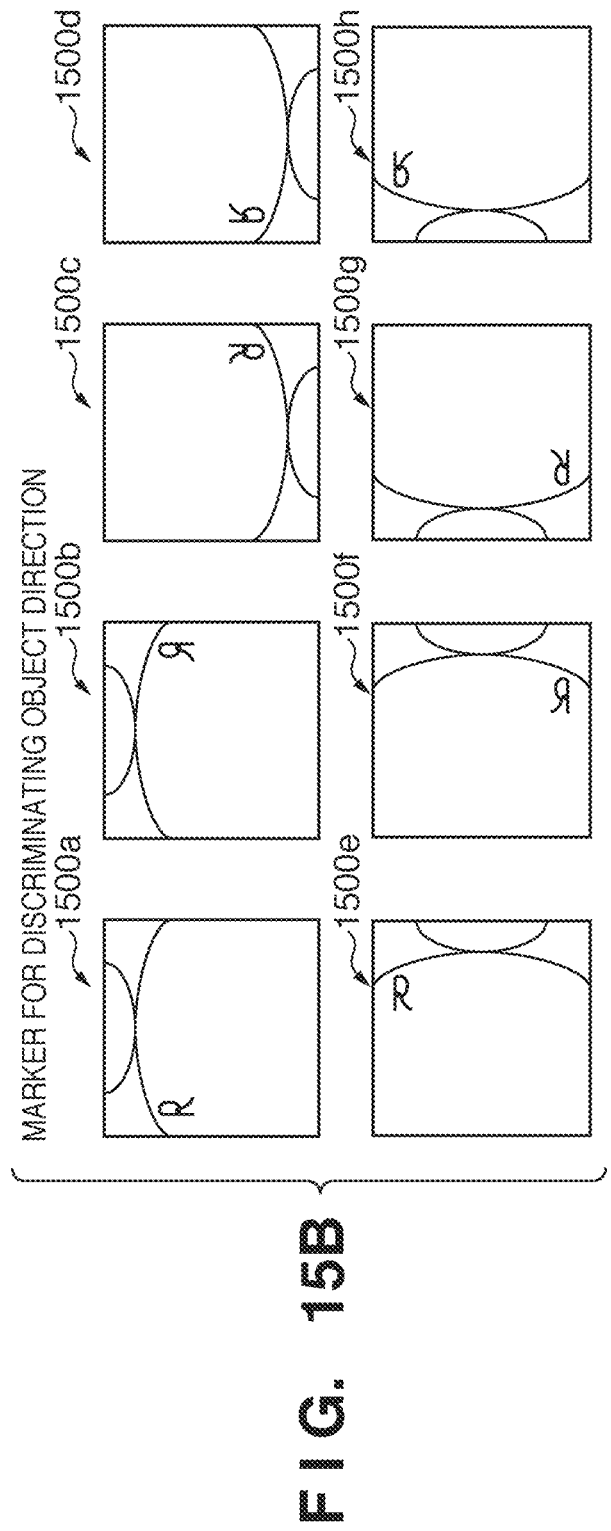

FIG. 12 is a view showing an example of the definitions of coordinate axes and reference vector when region="chest" and posture="lying" are set as an example of another object.

As shown in FIG. 12, in the case of an object 1200, coordinate axes 1201 are defined such that the central point of an object is set as the origin; the left half body side of the object, as the positive (+) side of the X-axis; the right half body side, as the negative (−) side of the X-axis; the head side, as the positive side of the Y-axis; the leg side, as the negative side of the Y-axis; the front side, as the positive side of the Z-axis, and the back side, as the negative side of the Z-axis.

In the case of the object 1200, a vector connecting the origin of the coordinate axes 1201 and coordinates (+1, +1, +1) is defined as a reference vector 1202 of the object (the chest in a lying state).

As described above, assume that in an X-ray detection apparatus 100, the coordinate axes and reference vectors of all objects are defined in advance.

In addition, in the first embodiment, in an operation procedure for setting information indicating an object direction, the operator operates the direction of the symbol 207 to match its direction with that of the object 701. However, the present invention is not limited to this.

It suffices to set postural information 125 in the X-ray detection apparatus 100 in advance and instruct the operator to match the direction of the object 701 with the postural information 125 set in the X-ray detection apparatus 100.

In addition, in the first embodiment, the postural information setting UI 101 and the postural information display UI 102 are configured to input a region, posture, and direction and display corresponding information. However, the present invention is not limited to this. For example, the embodiment may be configured to input and display other kinds of postural information.

Third Embodiment

The first embodiment has exemplified the case in which the postural information adding unit 106 superimposes an image of symbol data contained in the postural information 125 on the radiographed image data 128 and outputs the resultant data as the radiographed image data 132.

However, the present invention is not limited to this. For example, a postural information adding unit 106 may be configured to add postural information 125 as meta-data to the header of radiographed image data 128.

FIG. 13 is a view showing an example of the data format of radiographed image data 132 in this embodiment.

As shown in FIG. 13, the radiographed image data 132 includes a header 1301 and radiographed image 1302.

Information added to the header 1301 includes postural information 1303 containing information indicating an object direction, in addition to existing additional information such as the imaging time of the radiographed image 1302, its size, and various irradiation conditions at the time of X-ray imaging.

Reference numeral 1304 denotes an example of the description of the header 1301. Reference numerals 1300*a* to 1300*d* in FIG. 13 respectively denote cases in which the pieces of information indicating object directions (the coordinates of the reference vector of a symbol 207) respectively indicated by "(*a*)" to "(*d*)" in FIG. 10 are added to the respective headers.

Reference numeral 1305 denotes an example of the description of postural information 1303 contained in each description example 1304 of the header 1301.

In the example 1305, the data element "site" represents a region. If, for example, this value is "right_arm", it indicates that the region is "right arm". The value "chest" indicates that the region is "chest".

The data element "position" represents a posture. If, for example, the region is "right_arm" and the posture is "crooked_elbow", it indicates that the posture is "crooked elbow". If the posture is "uncrooked_elbow", it indicates that the posture is "uncrooked elbow".

The data elements "direction_x", "direction_y", and "direction_z" respectively represent the x-, y-, and z-coordinates of a reference vector 602 of the symbol 207 relative to coordinate axes 401.

As is obvious from the above description, this embodiment can perform processing such as displaying a radiographed image using the postural information on a monitor or the like by a desired display method at the time of diagnosis by adding radiographed image data to the postural information.

Fourth Embodiment

The first to third embodiments have exemplified the X-ray detection apparatus including the postural information setting UI and postural information display UI which respectively include a plurality of operation buttons for setting postural information and display areas to display pieces of postural information selected by the operation buttons.

However, the present invention is not limited to this. For example, the present invention may include a postural information setting UI including an object direction setting unit to set the postural information of an object by operating an operation member including a symbol representing a direction.

FIG. 14 is a view showing an example of a postural information setting UI 101 of an X-ray detection apparatus 100 according to the fourth embodiment of the present invention.

As shown in FIG. 14, the postural information setting UI 101 includes an object direction setting unit 1401.

The object direction setting unit 1401 is a spherical operation member in which a human-like symbol representing the direction of an object is drawn. The operator can set information indicating an object direction by rotating this sphere so as to match the direction of the embedded symbol with the direction of the object.

This embodiment uses the human-like symbol in the sphere as a symbol corresponding to an object. However, it is possible to use another symbol which can designate postural information, for example, a region of a body, an arrow, or a character string. In addition, this embodiment has exemplified the case in which the spherical object direction setting unit is used as an operation member. However, it is possible to use an object direction setting unit having another shape such as a rod-like shape or a circular shape.

Other Embodiments

Aspects of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (e.g., computer-readable medium).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2008-222792 filed Aug. 29, 2008, which is hereby incorporated by reference herein in its entirety.

What is claimed is:

1. An X-ray detection apparatus which detects X-rays irradiated to an object and generates a radiographed image of the object, the apparatus comprising:
   a detection area configured to detect the X-rays;
   a display unit configured to display, in a display area, a symbol which has a form corresponding to the object and for which a vector representing a direction as a reference for the symbol is defined, wherein said display area is arranged on the same side of the object as is said detection area;
   a changing unit configured to change the direction of the symbol displayed in the display area; and
   an output unit configured to output information concerning a direction of the vector relative to the X-ray detection apparatus in association with a radiographed image of the object, when said changing unit changes the direction of the symbol displayed in the display area to match the direction of the symbol displayed in the display area with the direction of the object.

2. The apparatus according to claim 1, wherein the vector is determined in advance for each of plural objects.

3. The apparatus according to claim 1, further comprising a setting unit configured to set a region and posture of an object,
   wherein said display unit displays, in the display area, a symbol corresponding to an object specified by a region and posture set by said setting unit.

4. The apparatus according to claim 1, wherein said output unit outputs an image of the symbol upon superimposing the image on the radiographed image, when said changing unit changes the direction of the symbol displayed in the display area to match the direction of the symbol displayed in the display area with the direction of the object.

5. The apparatus according to claim 1, wherein said output unit outputs information concerning a direction of the vector relative to the X-ray detection apparatus, as meta-data, upon adding the data to the radiographed image, when said changing unit changes the direction of the symbol displayed in the display area to match the direction of the symbol displayed in the display area with the direction of the object.

6. An information processing method in an X-ray detection apparatus which detects X-rays applied to an object and generates a radiographed image of the object, the method comprising the steps of:
   displaying, in a display area, a symbol which has a form corresponding to the object and for which a vector representing a direction as a reference for the symbol is defined, wherein the display area is arranged on the same side of the object as is a detection area which is configured to detect the X-rays;
   changing the direction of the symbol displayed in the display area; and
   outputting information concerning a direction of the vector relative to the X-ray detection apparatus in association with a radiographed image of the object, when the direction of the symbol displayed in the display area is changed in said step of changing to match the direction of the symbol displayed in the display area with the direction of the object.

7. An X-ray detection apparatus comprising:
an X-ray sensor configured to detect X-rays transmitted through an object;
a display unit configured to display, in a display area, a symbol representing a posture of the object;
a changing unit configured to change the symbol displayed in said display area; and
an output unit configured to output information concerning the symbol in association with radiographed image data based on the X-rays detected by said X-ray sensor.

8. The apparatus according to claim 7, wherein said output unit is communicatively connected to an X-ray image display apparatus.

9. The apparatus according to claim 7, wherein said output unit outputs the information concerning the symbol upon superimposing the information on the radiographed image data.

10. The apparatus according to claim 7, wherein the information concerning the symbol is added to a header of the radiographed image data.

\* \* \* \* \*